United States Patent [19]

Nagahama et al.

[11] 3,936,509

[45] Feb. 3, 1976

[54] PROCESS FOR SEPARATING DIMETHYL NAPHTHALENES COMPRISING 2,6-DIMETHYL NAPHTHALENES AS MAIN COMPONENT

[75] Inventors: Shizuo Nagahama; Keizo Shimada; Takeo Nishikawa, all of Hino; Toshiaki Harada, Hachioji, all of Japan

[73] Assignee: Teijin Limited, Osaka, Japan

[22] Filed: Nov. 4, 1974

[21] Appl. No.: 520,688

[52] U.S. Cl................................................ 260/674 N
[51] Int. Cl.² ....................................... C07C 7/01
[58] Field of Search ............................... 260/674 N

[56] References Cited
UNITED STATES PATENTS

| | | | |
|---|---|---|---|
| 2,941,017 | 6/1960 | Veatch et al. | 260/674 |
| 3,665,043 | 5/1972 | Davis et al. | 260/674 |
| 3,665,044 | 5/1972 | Scott | 260/674 |
| 3,665,045 | 5/1972 | Davis et al. | 260/674 |
| 3,725,490 | 4/1973 | Nagahama et al. | 260/674 |
| 3,812,198 | 5/1974 | Hedge | 260/674 |

Primary Examiner—Delbert E. Gantz
Assistant Examiner—C. E. Spresser
Attorney, Agent, or Firm—J. Edward Hess; Donald R. Johnson

[57] ABSTRACT

A process for separating dimethyl naphthalenes having a component comprising 2,6-dimethyl naphthalene in the form of complexes with a complex-forming compound, which comprises contacting a dimethyl naphthalene isomer mixture comprising at least 2,6-dimethyl naphthalene or a hydrocarbon mixture containing said dimethyl naphthalene isomer mixture with a complex-forming compound selected from the group consisting of nitro compounds of 2,6-naphthalene dicarboxylic acid, trimellitic anhydride and 2-chloro-5-nitrobenzoic acid, thereby to form a mixture of complexes of the dimethyl naphthalenes with said complex-forming compound having a main component comprising a complex of 2,6-dimethyl naphthalene with the complex-forming compound, and separating the complexes in the solid state from the reaction mixture.

2 Claims, No Drawings

PROCESS FOR SEPARATING DIMETHYL NAPHTHALENES COMPRISING 2,6-DIMETHYL NAPHTHALENES AS MAIN COMPONENT

This invention relates to a process for separating dimethyl naphthalenes comprising 2,6-dimethyl naphthalene as a main component in the form of their complexes with a complexforming compound, which comprises contacting a mixture of isomers of dimethyl naphthalene (abbreviated as "DMN" hereinbelow) containing at least 2,6-dimethyl naphthalene (abbreviated as "2,6-DMN" hereinbelow) or a hydrocarbon mixture containing such isomeric mixture with a complex-forming compound selected from the group consisting of a nitro-compounds of 2,6-naphthalene dicarboxylic acids, trimellitic anhydride and 2-chloro-5-nitrobenzoic acid.

2,6-DMN can be converted to naphthlene-2,6-dicarboxylic acid by oxidation, and the resulting naphthalene-2,6-dicarboxylic acid is useful as the starting material for the preparation of polyesters and plasticizers.

Also other DMN isomers such as 1,5-DMN and 1,6-DMN can be converted to naphthalene-2,6-dicarboxylic acid by oxidizing them and then subjecting the oxidized products to the so-called Henkel rearrangement reaction.

Accordingly, various proposals have been made to separate DMN mixtures comprising 2,6-DMN in the highly concentrated state from a mixture of DMN isomers comprising 2,6-DMN or a hydrocarbon mixture containing such mixture of DMN isomers.

For instance, a DMN mixture comprising 2,6-DMN and 2,7-DMN as main components can be obtained by cooling a DMN-containing fraction concentrated and extracted from a petroleum or coal tar starting material by a suitable method. The resulting DMN mixture is recrystallized from a suitable solvent. This recrystallizing method is disclosed in, for instance, U.S. Pat. No. 3,249,644. In U.S. Pat. No. 3,485,885 and U.S. Pat. No. 3,400,548 a partially melting process is proposed comprising melt-separating low melting point components of the above DMN mixture or a low melting point eutectic mixture, from such DMN mixture derived from a petroleum or coal tar starting material. By adopting these methods or a combination of these methods 2,6-DMN can be separated but the yield of 2,6-DMN is very low.

2,6-DMN and 2,7-DMN form a eutectic mixture at a molar ratio of 41.5:58.5, and 2,6-DMN and 2,3-DMN form a eutectic mixture at a molar ratio of 47.5:52.5. Accordingly, if the starting DMN mixture contains 2,7-DMN of 2,3-DMN as well as 2,6-DMN, a eutectic mixture of 2,6-DMN with 2,7- or 2,3-DMN is formed and it is impossible to separate 2,6-DMN from the starting mixture in which such eutectic mixture has been formed, by the above recrystallizing or partially melting method. In an ordinary starting mixture, for instance, 2,6-DMN is contained at a content of about 11 – 12% by weight, and 2,7-DMN is contianed at a similar content. In starting mixture, about 4/6 mole of 2,6-DMN per mole of 2,7-DMN forms a eutectic mixture with 2,7-DMN present in the starting mixture. Accordingly, the 2,6-DMN which can be actually separated is at most 30% or less of the entire 2,6-DMN present in the starting mixture, and although it is possible to increase the content of 2,6-DMN by fractional rectification up to about 30%, since the boiling point of 2,7-DMN is very close to the boiling point of 2,6-DMN the proportions of 2,6-DMN and 2,7-DMN can not be changed greatly. Therefore, the yield of pure 2,6-DMN cannot be increased by the above recrystallizing or partially melting method.

With a view to overcoming the disadvantages of the above methods, it was proposed to separate DMN in the form of a complex of it with a compound capable of forming a complex. For example, U.S. Pat. No. 3,665,043 discloses a method in which pyromellitic anhydride is used as the complex-forming compound. The pyromellitic anhydride, however, has the property of selectively forming a complex with 1,5-DMN, and is unsatisfactory when it is desired to separate 2,6-DMN selectively in the form of its complex. Furthermore, since 1,5-DMN is in the form of crystals having a melting point of 82°C., and forms a eutectic mixture with 2,6-DMN in a ratio of 66:34, difficulties will be encountered when the resulting complex is heat-melted at reduced pressure to separate 2,6-DMN. Thus, pyromellitic anhydride is unsuitable as a complex-forming compound for the separation of 2,6-DMN.

U.S. Pat. No. 3,665,044 discloses a method in which 2-chloro-4-nitrobenzoic acid is used as a complex-forming compound for the separation of DMN. However, the 2-chloro-4-nitrobenzoic acid has the property of forming a complex selectively with 1,6-DMN and is unsuitable for selectively separating 2,6-DMN.

On the other hand, U.S. Pat. No. 3,725,490 discloses a method in which m-nitrobenzoic acid is utilized as a complex-forming compound. This method involves contacting a dimethyl naphthalene isomer mixture comprising at least 2,6-dimethyl naphthalene or a hydrocarbon mixture containing said dimethyl naphthalene isomer mixture with m-nitrobenzoic acid thereby to form a mixture of complexes of the dimethyl naphthalenes with m-nitrobenzoic acid having a main component comprising a complex of 2,6-dimethyl naphthalene with m-nitrobenzoic acid, and separating the complexes in the solid state from the reaction mixture.

As a result of our work on the improvement of the method for separating 2,6-DMN, we found that a compound selected from the group consisting of nitro-compounds of 2,6-naphthalenedicarboxylic acid, trimellitic anhydrie and 2-chloro-5-nitrobenzoic acid selectively forms a complex with 2,6-DMN.

It has also been found that these complex-forming compounds can selectively form more complexes with 2,6-DMN when used in lesser amounts than in the case of m-nitrobenzoic acid disclosed in U.S. Pat. No. 3,725,490. The m-nitrobenzoic acid forms a complex with DMN in a mol ratio of 2:1, whereas the two complex-forming compounds used in this invention, namely trimellitic anhydride and 2-chloro-5-nitrobenzoic acid, form complexes in a mol ratio of 1:1., Therefore, these complex-forming compounds used in this invention selectively form complexes with 2,6-DMN with very good efficiency.

Furthermore, the complex-forming compounds used in this invention have lower solubility in DMN than m-nitrobenzoic acid has. The solubility of m-nitrobenzoic acid at room temperature is about 2%, whereas the solubilities of 2-chloro-5-nitrobenzoic acid, trimellitic anhydride, and a nitro compound of 2,6-naphthalenedicarboxylic acid, e.g., its dinitro compound are about 1%, 0.2%, and less than 0.1%, respectively. Hence, the loss of the complex-forming compound as a result of dissolution in the mother liquor after separation of 2,6-DMN complex is reduced. We further found that when separating 2,6-DMN from the resulting 2,6-DMN complex, the amount of the complex-forming compound to be mixed in the 2,6-DMN solvent solution is small, and 2,6-DMN of high purity can be obtained.

Accordingly, it is a primary object of this invention to provide an improved process by which a DMN mixture containing 2,6-DMN in a very high concentration can be separated in high yield from a mixture of isomers of DMN.

Another object of this invention is to provide an improved process by which a DMN mixture containing 2,6-DMN in a very high concentration can be separated in high yield from a hydrocarbon mixture comprising 2,6-DMN and one or more other DMN isomers.

Other objects and advantages of this invention will be apparent from the following description.

According to this invention a process is provided for separating DMN the main component of which is 2,6-DMN in the form of their complexes with a complex-forming compound, which comprises contacting a DMN isomer mixture comprising at least 2,6-DMN or a hydrocarbon mixture containing such DMN isomer mixture with a complex-forming compound selected from the group consisting of nitro-compounds of 2,6-naphthalenedicarboxylic acid, trimellitic anhydride, and 2-chloro-5-nitrobenzoic acid, thereby to form a mixture of complexes of the DMN with said complex-forming compound the main component of which is a complex of 2,6-DMN with the complex-forming compound, and separating the complexes in the solid state from the reaction mixture.

In general, mixtures of DMN isomers and hydrocarbon mixtures comprising such isomeric mixture are liquid at room temperature. When these mixtures are allowed to contact with a complex-forming compound selected from the group consisting of nitro compounds of 2,6-naphthalenedicarboxylic acid, trimellitic anhydride and 2-chloro-5-nitrobenzoic acid in accordance with this invention, the complex-forming compound forms solid complexes selectively with 2,6- and 2,7-DMN, especially with 2,6-DMN. The resulting solid complexes can be separated easily from the liquid mixture by a known liquid-solid separation technique such as filtration and centrifugal separation.

Of the complex-forming compounds used in the present invention, trimellitic anhydride is most preferred. The nitrocompounds of 2,6-naphthalenedicarboxylic acid include, for example, mono-, di-, tri-nitro compounds and mixtures thereof. Of these, the di-nitro compounds are especially preferred, and the dinitrocompound alone or a mixture of it with the dinitrocompound can be utilized preferably. The mixture preferably contains at least 80%, based on the weight of the mixture, of the di-nitro compound. The mixture can be used without any trouble even if it contains 2,6-naphthalenedicarboxylic acid which is a starting material for the synthesis of the nitro compound. Accordingly, the nitration reaction mixture of 2,6-naphthalenedicarboxylic acid can be directly used. Desirably, however, the unreacted 2,6-naphthalenedicarboxylic acid is removed as much as possible by, for example, recrystallization. This is preferable in order to increase the efficiency of adsorption, and to utilize an adsorption-separation device effectively.

In this invention any DMN isomer mixture comprising at least 2,6-DMN can be used as a starting material. Hydrocarbon mixtures containing a DMN isomer mixture comprising at least 2,6-DMN can also be used. For example, a 250° – 270°C. fraction obtained from coal tar comprises about 5-10% by weight of 2,6-DMN, about 5–10% by weight of 2,7-DMN, 45-55% by weight of other DMN isomers, and various aromatic compounds such as biphenyl monomethyl naphthalene, and monoethyl naphthalene. Further, a 250° – 270°C. aromatic fraction extracted from the reaction product obtained by the the thermal cracking of a 200° – 300°C. petroleum fraction comprises about 8–13% of 2,6-DMN, about 8–13% of 2,7-DMN, about 50–60% of other DMN isomers and about 10–20% of other aromatic compounds. In addition, various mixtures of DMN isomers comprising 2,6-DMN are contained in bottom oils of petroleum reformers.

In accordance with this invention, any aliphatic, alicyclic or aromatic hydrocarbon mixture containing a mixture of DMN isomers comprising at least 2,6-DMN, such as those mentioned above, can be used.

Even when the starting material to be used in this invention contains small amounts, for example, less than about 10%, of a nitrogen-containing compound such as quinoline and indole and a sulfur-containing compound such as thionaphthene, no particular disadvantage is brought about.

According to this invention, the DMN isomer mixture comprising at least 2,6-DMN or the hydrocarbon mixture containing said dimethyl naphthalene isomer mixture is contacted with the complex-forming compound in a manner such that the isomeric mixture or hydrocarbon mixture is kept in the liquid state during the contact. Accordingly, when the starting mixture is solid at room temperature, it may be heated to melt it, or an aliphatic, alicyclic or aromatic hydrocarbon having a low boiling point is added to form a liquid system. It is also possible to heat such a liquid system formed by the addition of the low boiling hydrocarbon. During the contact, the complex-forming compound may be either in the solid state or in the liquid state. In order, however, to complex the complex-forming reaction in a short period of time, it is preferable to add the complex-forming compound to the starting isomeric mixture or hydrocarbon mixture and mix them in the liquid state under heat. The complex-forming reaction can be carried out at room temperature to 150°C., preferably from room temperature to 70°C.

When the reaction is carried out while maintaining both in the dissolved state as described above, the resulting liquid reaction mixture is cooled, and the precipitated solid is separated from the reaction mixture. The precipitated solid is composed of complexes of the complex-forming compound with isomers of DMN containing as a main component a complex of the complex-forming compound with 2,6-DMN. It is sufficient that cooling is carried out to an extent which leads to the formation of solid precipitates.

The complex-forming reaction in this invention can be performed in various modes. For example, there can be employed a batchwise method in which the DMN isomer mixture comprising at least 2,6-DMN or the hydrocarbon mixture containing the above DMN isomer mixture is mixed in a suitable ratio with the complex-forming compound in a vessel of appropriate capacity, and the mixture is stirred to form complexes, a method in which the above-mentioned starting material is passed through a column packed with the complex-forming compound, and a method in which the starting material is introduced from the bottom of a cylindrical reaction tube and the complex-forming compound is added from the top of the tube to bring them into a continuous countercurrent contact with each other. Hence, the ratio between the above starting material and the complex-forming compound may be any ratio, and can be changed optionally according to the method employed.

In accordance with this invention, the mixture of complexes of the complex-forming compound with DMN isomers, the main component of which is the 2,6-DMN complex, is precipitated in the form of stable solid crystals preferably by cooling it appropriately. The cooling temperature is determined according to the desired amount of the precipitated crystals. In general, the precipitation is performed preferably at a temperature lower by at least 5°C. than the temperature employed in the complex-forming reaction and within a range of from room temperature to 110°C., preferably to 70°C. Of course, no particular disadvantage arises if the precipitation of solid crystals is effected at a temperature a little lower or higher than the above range.

Precipitated crystals can be separated from the liquid reaction mixture by an optional solid-liquid separating technique, such as filtration and centrifugal separation. The separated complex may be purified, if desired. In order to purify the precipitated crystals, they are preferably washed with a solvent selected from the group consisting of aromatic hydrocarbons, aliphatic hydrocarbons, alicyclic hydrocarbons, ethers, esters, alcohols and ketones. Examples of the aromatic hydrocarbons are those of 6 to 9 carbon atoms, such as benzene, toluene, xylene, trimethyl benzene, ethyl benzene, methyl benzene and cumene. Examples of the aliphatic hydrocarbons are those of 6 to 10 carbon atoms such as hexane, heptane, octane, nonane and decane. Examples of the alicyclic hydrocarbons are those of 6 to 10 carbon atoms such as cyclohexane and decalin. Examples of the ethers are diethyl ether, diisopropyl ether, tetrahydrofuran and dioxane. The alcohols are preferably methanol, ethanol and isopropanol. Acetone and methyl ethyl ketone are especially preferred as the ketone. Ethyl acetate is most preferred as the ester. Mixtures of two or more of the above solvents can also be used.

When the amount of the above organic solvent used for purification is large, the complex partly decomposes, and DMN separates. Hence, purification and decomposition can be performed simultaneously.

In order to decompose a mixture of complexes consisting of the complex-forming compound of this invention and DMN isomers, which has thus been obtained in accordance with this invention and contains as a main component a complex of the complex-forming compound with 2,6-DMN, to a mixture of DMN isomers and the complex-forming compound, it is preferable to use the following four methods in the main.

A. A method comprising heating the mixture of complexes at a temperature not lower than 50°C. but preferably up to the composition point of the complex-forming compound (which will be referred to as "decomposition method A" hereinbelow).

B. A method comprising contacting a mixture of complexes with a solvent which hardly dissolves the complex-forming compound but dissolves DMN well (which will be referred to as "decomposition method B" hereinbelow).

C. A method comprising contacting a mixture of complexes with a solvent which hardly dissolves DMN but dissolves the complex-forming compound well (which will be referred to as "decomposition method C" hereinbelow).

D. A method comprising contacting a mixture of complexes simultaneously or alternately with the solvents used in the above methods B and C which are immiscible with each other (which will be referred to as "decomposition method D" hereinbelow).

DECOMPOSITION METHOD A

One example of the decomposition method A comprises heating a mixture of complexes at a temperature not lower than 50°C., preferably in an atmosphere of an inert gas. Although the decomposition can be accomplished by heating the complex mixture at a temperature not lower than 50°C. in the air, the heating is preferably done in an atmosphere of an inert gas such as nitrogen, carbon dioxide gas, hydrogen and a lower hydrocarbon, e.g., methane and ethane, because the heating in an oxidizing atmosphere results in a tendency that the resulting mixture of DMN isomers contains 2,6-DMN as a main component is colored or decomposed. In the above decomposition, steam can be used instead of the inert gas.

When heating the complex mixture preferably in an inert gas atmosphere, the heating temperature can be raised above the distillation or sublimation temperature of the mixture thereby to recover a DMN mixture composed mainly of 2,6-DMN simultaneously with the decomposition of the complex mixture according to a distillation or sublimation technique.

Further, when decomposing the complex by method A, the complex mixture can be heated at a temperature higher than 50°C. in a solvent to be used in the decomposition method B, C or D, which will be described below in detail.

The upper limit of the heating temperature is the decomposition temperature of 2,6-DMN, and any temperatures not lower than 50°C. but up to the decomposition temperature of 2,6-DMN can be used. However, in order to recover and reuse the complex-forming compound of this invention, heating is carried out preferably at a temperature lower than the decomposition temperature of the complex-forming compound. Especially preferred heating temperatures are 70° to 50°C.

DECOMPOSITION METHOD B

The decomposition method B comprises contacting the complex mixture intimately with a solvent which hardly dissolves the complex-forming compound but dissolves DMN well. Suitable solvents include, for example, aliphatic, alicyclic or aromatic hydrocarbons containing 3 to 10 carbon atoms, especially 3 to 8 carbon atoms, those saturated being particularly preferred, such as propane, butane, petroleum ether, pentane, hexane, heptane, octane, decalin, ligron, cyclopentane and cyclohexane. The amount of the solvent is not critical, but as the amount of the complex-forming compound sissolved increases in proportion to the amount of the solvent used, it is preferred to use the solvent in a smaller amount, for example, 0.5 to 10 parts by weight per part by weight of the complex mixture to be decomposed.

The complex-forming compound dissolved in the solvent can be removed by extraction with hot water after the decomposition treatment.

In order to decompose the complex mixture by contacting it with such a solvent, the system is preferably heated at a temperature not lower than 50°C. but up to the decomposition temperature of 2,6-DMN, especially up to the decomposition temperature of the complex-forming compound. Especially preferred temperatures are 70° to 150°C., as described with respect to the decomposition method A.

DECOMPOSITION METHOD C

According to this decomposition method C, the complex mixture is decomposed by contacting it with a solvent which hardly dissolves DMN but dissolves the complex-forming compound well. Preferred solvents are, for example, water (hot water), and alkaline aqueous solutions. The use of alkaline aqueous solutions is most preferred because they have the ability to decompose the complex mixture completely.

In this method, complex forming compounds are recovered as their alkaline salt. Addition of a mineral acid or carbon dioxide gas to the recovered product permits it to be recovered as a free acid.

Water-soluble hydroxides, oxides and carbonates of alkali metals and alkaline earth metals, aqueous ammonoa, and water-soluble amines can, for example, be used to form the alkaline aqueous solutions. The use of aqueous ammonia is especially preferred.

In this method C, the temperature conditions as described with respect to the decomposition method B can be similarly applied. However, if an alkaline aqueous solution is used, the complex can be decomposed very smoothly at a temperature lower than 50°C., for example, at room temperature.

The amount of the solvent used is not particularly critical.

DECOMPOSITION METHOD D

In this method, at least one solvent described with regard to the method B and at least one solvent described with regard to the method C, which are immiscible with each other, are used, and the complex mixture is contacted with them simultaneously or alternately.

Preferably, a mixture is used which consists of (i) at least one saturated hydrcarbons containing 3 to 10 carbon atoms, especially 3 to 8 carbon atoms, such as described with regard to the decomposition method B and (ii) at least one solvent selected from water and alkaline aqueous solutions.

As stated above, the amount of the solvent (ii) is not particularly critical, while it is preferred to use the solvent (i) in an amount of 0.3 to 5 parts by weight, especially 0.5 to 3 parts by weight, per part by weight of the complex mixture.

When the complex mixture is decomposed by this method D, the solvents (i) and (ii) are placed in a decomposition vessel, a suitable amount of the complex mixture is added thereto, and the mixture is well blended and agitated. When water is used as the solvent (ii), the system is preferably heated at a temperature of 70° to 150°C. When an alkaline aqueous solution is used as the solvent (ii), heating is unnecessary.

Preferably, the agitation is performed until both of the solvents (i) and (ii) become clear. By using this procedure, the complex mixture is decomposed to a DMN mixture composed mainly of 2,6-DMN which is substantially dissolved in the layer of the saturated hydrocarbon (i).

The DMN mixture composed mainly of 2,6-DMN can be separated and recovered by distilling off a part of the solvent from the layer of the solvent (i), and then cooling it, or by distilling off substantially the whole of the solvent (i).

The DMN mixture so recovered which contains 2,6-DMN as a main component can, if desired, be purified by the abovementioned crystallizing or known purification method.

The following Examples illustrate the invention in greater detail.

EXAMPLE 1

20 parts of trimellitic anhydride was added to 40 parts of a crude DMN fraction of the composition shown in the 2nd column of Table 1. The mixture was allowed to stand for 2 hours at room temperature, filtered, and washed with petroleum ether to afford 36.2 parts of a complex. The resulting mother liquor was combined with the residue resulting from the removal of the petroleum ether from the washed filtrate by evaporation (the combined mixture will be referred to as "filtrate" for simplicity). The amount of the filtrate obtained was 23.8 parts. The complex was then dispersed in water, and heated to distill DMN together with steam to afford 16.3 parts of a DMN mixture and 20 parts of trimellitic acid. The compositions of the filtrate and the DMN mixture separated from the complex are shown in the third and fourth columns of Table 1. The composition was determined by gas-chromatography. Thus, 80% of 2,6-DMN contained in the starting material was separated as a complex. The proportion of DMN in the complex was 45%. On the other hand, 76% of 2,6-DMN was separated as a complex using m-nitrobenzoic acid in an amount half of that of the starting material. The proportion of DMN in the complex was about 25%. This shows that when used in the same amount, trimellitic anhydride could separate DMN and 2,6-DMN with better efficiency than m-nitrobenzoic acid.

EXAMPLE 2

20 parts of trimellitic anhydride was added to 80 parts of the same DMN fraction as used in Example 1. The mixture was stirred for 2 hours at room temperature, filtered, and washed with 20 parts of petroleum ether to afford 35.9 parts of a complex. The complex was placed in a separatory funnel, and shaken upon addition of 50 parts of ether and a 10% aqueous solution of sodium hydroxide. As a result, the hydrocarbons moved to the ether phase. Ether was evaporated off from the ether phase to afford 16.1 parts of a DMN mixture. The filtrate weighed 64.1 parts, and contained 0.2% of trimellitic anhydride dissolved therein.

The compositions of the filtrate and the DMN mixture separated from the complex are shown in the 5th and 6th columns of Table 1.

Table 1

| Example No. | Starting material (wt.%) | Example 1 Filtrate (wt.%) | Example 1 DMN mixture separated from the complex (wt.%) | Example 2 Filtrate (wt.%) | Example 2 DMN mixture separated from the complex (wt.%) |
| --- | --- | --- | --- | --- | --- |
| Ethylnaphthalene | 5.0 | 7.6 | 1.3 | 6.0 | 1.0 |
| 2,6-DMN | 12.1 | 4.1 | 23.8 | 7.1 | 32.0 |
| 2,7-DMN | 12.0 | 13.6 | 9.7 | 13.3 | 6.8 |
| 1,7-DMN | 12.8 | 10.6 | 16.0 | 12.7 | 13.2 |
| 1,6-DMN | 18.6 | 12.6 | 27.3 | 16.2 | 28.0 |
| 1,3-DMN | 12.1 | 14.7 | 8.3 | 14.1 | 4.3 |
| 2,3-DMN | 4.8 | 3.9 | 6.1 | 4.9 | 4.5 |
| 1,4-DMN | 2.0 | 2.6 | 1.1 | 2.2 | 1.2 |
| 1,5-DMN | 2.3 | 2.9 | 1.5 | 2.6 | 1.1 |
| 1,2-DMN | 2.6 | 1.4 | 4.4 | 2.4 | 3.5 |
| 1,8-DMN | 0.4 | 0.5 | 0.2 | 0.5 | 0.1 |

EXAMPLE 3

10 parts of 2-chloro-5-nitrobenzoic acid was added to 32 parts of a crude DMN fraction of the composition shown in the 2nd column of Table 2. The mixture was stirred for 3 hours at room temperature, filtered, and washed with petroleum ether to afford 17.6 parts of a complex. The complex was decomposed with steam to afford 7.9 parts of a DMN mixture. The filtrate weighed 24.4 parts, and contained 0.3 part of the 2-chloro-5-nitrobenzoic acid.

The compositions of the starting materials, the filtrate and the separated DMN mixture are shown in Table 2.

EXAMPLE 4

12 parts of 2-chloro-5-nitrobenzoic acid was added to 100 parts of a starting DMN mixture of the same composition as used in Example 3, and the mixture was stirred for one hour at room temperature. The mixture was filtered, and washed with 10 parts of petroleum ether to form 20.3 parts of a comlex. The filtrate weighed 91.7 parts, and contained 0.9 part of the 2-chloro-5-nitrobenzoic acid. The composition of the filtrate is shown in the 5th column of Table 2.

The complex was decomposed in the same way as in Example 2 to afford 9.2 parts of a DMN mixture which had the composition shown in the 6th column of Table 2. The composition was determined by gas-chromatography.

When the DMN mixture separated from the complex was recrystallized with methanol, 4.1 parts of 2,6-DMN having a purity of 99.3% was obtained.

EXAMPLE 5

200 parts of a dinitro compound of 2,6-naphthalenedicarboxylic acid was added to 280 parts of a crude DMN fraction of the composition shown in the second column in Table 3 below, the mixture was stirred for 3 hours at room temperature, and filtered, followed by washing with 70 parts of petroleum ether to form 243.5 parts of a complex. The filtrate weighed 229 parts and contained 0.03 part of dinitro 2,6-naphthalene dicarboxylic acid. The composition of this filtrate is shown in the third column of Table 3. The resulting complex was decomposed as Example 2 to obtain 43.6 g of the DMN mixture. The composition of the resulting DMN mixture is shown in the fourth column of Table 3.

EXAMPLE 6

40 parts of a dinitro compound of 2,6-naphthalenedicarboxylic acid was added to a mixture of 50 parts of a starting DMN as used in Example 5 and 450 parts of o-xylene. The mixture was stirred for 5 hours at room temperature, filtered, and washed with petroleum ether to obtain 48 parts of a complex. In the same way as in Example 5, the complex was decomposed with an alkali aqueous solution, and DMN was extracted with ether. Ether was evaporated off from the ether phase to afford 9.9 parts of a DMN mixture. The compositions of the filtrate and the DMN separated are shown in the 5th and 6th column of Table 3.

Table 2

| Example No. | Starting DMN (wt.%) | Example 3 Filtrate (wt.%) | Example 3 DMN mixture separated from the complex (wt.%) | Example 4 Filtrate (wt.%) | Example 4 DMN separated from the complex (wt.%) |
| --- | --- | --- | --- | --- | --- |
| Mononuclear aromatics | 16.3 | 20.0 | 4.3 | 18.6 | 2.1 |
| Ethylnaphthalene | 4.0 | 5.1 | 0.8 | 4.7 | 0.5 |
| 2,6-DMN | 12.0 | 4.7 | 39.9 | 7.5 | 58.7 |
| 2,7-DMN | 11.9 | 9.6 | 20.8 | 11.1 | 20.1 |
| Other DMN | 54.9 | 59.7 | 34.0 | 56.7 | 18.0 |
| Others | 1.4 | 1.3 | 0.2 | 1.4 | 0.6 |

Table 3

| Example No. | Starting material (wt.%) | Example 5 | | Example 6 | |
|---|---|---|---|---|---|
| | | Filtrate (wt.%) | DMN mixture separated from the complex (wt.%) | Filtrate (wt.%) | DMN separate from the complex (wt.%) |
| Mononuclear aromatics | 16.3 | 19.2 | 1.8 | 20.9 | 0.1 |
| Ethylnaphthalene | 4.0 | 4.9 | — | 5.1 | — |
| 2,6-DMN | 12.2 | 7.1 | 39.1 | 4.0 | 45.9 |
| 2,7-DMN | 11.9 | 11.2 | 19.2 | 6.2 | 35.0 |
| Other DMNs | 54.4 | 56.5 | 41.5 | 62.5 | 18.6 |
| Others | 1.2 | 1.2 | 0.3 | 1.2 | 0.2 |

EXAMPLE 7

125.0 parts of an o-xylene solution containing 25% of a starting crude DMN of the composition shown in the second column of Table 4 and 10.0 parts of a dinitro compound of 2,6-naphthalenedicarboxylic acid were stirred for 4 hours at room temperature. The mixture was treated in the same way as in Example 5 to form 14.6 parts of a complex. The complex was decomposed with alkali in the same way as in Example 5 to form 5.3 parts of a DMN mixture. The compositions of the filtrate and DMN separated are shown in the third and fourth columns of Table 4.

Table 4

| | Starting DMN (wt.%) | Filtrate (wt.%) | DMN separated from the complex (wt.%) |
|---|---|---|---|
| Mononuclear aromatic | 5.9 | 7.3 | 0.6 |
| Ethylnaphthalene | — | — | — |
| 2,6-DMN | 58.5 | 50.5 | 90.0 |
| 2,7-DMN | 17.4 | 20.5 | 5.5 |
| Other DMNs | 17.7 | 21.3 | 3.9 |
| Others | 0.4 | 0.4 | 0.1 |

EXAMPLES 8 and 9

250 Parts of an o-xylene solution containing 10% of the same starting DMN as used in Example 5 was mixed with 20 parts of a dinitro compound of 2,6-naphthalenedicarboxylic acid, and the mixture was stirred for 2 hours at room temperature, and filtered to form 23.4 parts of a complex.

11.7 parts of the complex was neutralized with a 5% aqueous solution of sodium hydroxide, and DMNs were extracted using ether. Ether was evaporated off from the ether phase to form 2.0 parts of a DMN mixture. The composition of the DMN mixture is shown in the fourth column of Table 5 below. (Example 8).

The remaining half (11.7 parts) of the complex was mixed with 200 parts of heptane, and heated to 80°C., after which the mixture was filtered. The precipitate was washed twice with 14 parts of hot heptane. Heptane was evaporated off to form 1.96 parts of a DMN mixture which had the composition shown in the fifth column of Table 5. (Example 9-1)

Then, the complex after washing with heptane was neutralized with a 5% aqueous solution of alkali, and extracted with ether. Ether was evaporated off from the ether phase to afford 0.03 parts of a DMN mixture which had the composition shown in the sixth column of Table 5. (Example 9-2)

It can be seen from the results that 98% of DMN in the complex was separated by means of hot heptane.

Table 5

| | Starting DMN (wt.%) | Filtrate (wt.%) | Example 8 (wt.%) | Example 9-1 (wt.%) | Example 9-2 (wt.%) |
|---|---|---|---|---|---|
| Mononuclear aromatic | 16.3 | 18.5 | 3.8 | 3.8 | — |
| Ethylnaphthalene | 4.0 | 4.5 | — | — | — |
| 2,5-DMN | 12.2 | 5.7 | 46.1 | 44.8 | 58.6 |
| 2,7-DMN | 11.9 | 9.6 | 23.9 | 24.8 | 41.4 |
| Other DMNs | 54.4 | 60.8 | 25.8 | 26.2 | |
| Others | 1.2 | 9.9 | 0.4 | 0.4 | |

What we claim is:

1. A process for separating dimethyl naphthalenes having a component comprising 2,6-dimethyl naphthalene in the form of complexes with a complex-forming compound, which comprises contacting a dimethyl naphthalene isomer mixture comprising at least 2,6-dimethyl naphthalene or a hydrocarbon mixture containing said dimethyl naphthalene isomer mixture with a complex-forming compound selected from the group consisting of nitro compounds of 2,6-naphthalene dicarboxylic acid, trimellitic anhydride and 2-chloro-5-nitrobenzoic acid, thereby to form a mixture of complexes of the dimethyl naphthalenes with said complex-forming compound having a main component comprising a complex of 2,6-dimethyl naphthalene with the complex-forming compound, and separating the complexes in the solid state from the reaction mixture.

2. The process of claim 1 wherein the dimethyl naphthalene isomer mixture comprising at least 2,6-dimethyl naphthalene or the hydrocarbon mixture containing said dimethyl naphthalene isomer mixture is contacted in the liquid state with said complex-forming compound.

* * * * *